United States Patent [19]
Oda

[11] Patent Number: 5,707,825
[45] Date of Patent: Jan. 13, 1998

[54] INTERFACE BIOREACTOR SYSTEM

[75] Inventor: Shinobu Oda, Hiratsuka, Japan

[73] Assignee: Kansai Paint Co., Ltd., Hyogo, Japan

[21] Appl. No.: 686,691

[22] Filed: Jul. 26, 1996

[30] Foreign Application Priority Data

Jul. 28, 1995 [JP] Japan .................. 7-211405

[51] Int. Cl.$^6$ .................. C12P 1/00; C12M 1/00
[52] U.S. Cl. .................. 435/41; 435/170; 435/248; 435/249; 435/296.1
[58] Field of Search .................. 435/6, 286, 299, 435/300, 310, 311, 313, 315, 176, 177, 312, 240.23, 284, 288, 246, 148, 290, 285, 41, 170, 298, 296.1; 210/603, 610

[56] References Cited

U.S. PATENT DOCUMENTS 5,075,234 12/1991 Tunac .................. 435/286

*Primary Examiner*—James Ketter
*Assistant Examiner*—Irem Yucel
*Attorney, Agent, or Firm*—Wenderoth, Lind & Ponack

[57] ABSTRACT

This invention provides an interface bioreactor system comprising (a) a reaction tank having (1) a reaction solvent placed therein, (2) a plurality of plate-like hydrophilic immobilizing carriers each having a thickness of 1 to 500 mm and packed therein so as to be arranged in a vertical position at intervals of 3 to 100 mm, the hydrophilic immobilizing carriers having a microorganism deposited and immobilized on the surfaces thereof in a growable or viable state and containing a liquid medium composed of water and nutrients necessary for the growth or survival of the microorganism, and (3) a sparger or agitator disposed at the bottom thereof; and (b) an aeration line connected with the reaction tank for supplying oxygen thereto. This system is highly efficient and can be scaled up easily.

10 Claims, 1 Drawing Sheet

INTERFACE BIOREACTOR SYSTEM

This invention relates to an interface bioreactor system for the microbial transformation of raw materials which are insoluble or slightly soluble in water.

BACKGROUND OF THE INVENTION

Conventionally, techniques for converting inexpensive water-soluble raw materials into useful substances with the aid of microorganisms have been used for the production of optically active compounds typified by raw materials for the manufacture of, in particular, drugs, agricultural chemicals and electronic materials [H. Ohta, Yukigoseikagaku (in Japanese), 14, 823 (1983); Fujisawa et al., Yukigoseikagaku (in Japanese), 44, 519 (1986); H. Ohta, Bioscience and Industry (in Japanese), 44, 823 (1991)]. Meanwhile, a number of methods for the microbial transformation of water-insoluble raw materials have been proposed. They include, for example, the emulsion or surfactant addition method in which the low solubility and dispersibilty of a raw material is compensated for by dispersing it in water through forced agitation [T. Nakahara et al., J. Ferment. Technol., 59, 415 (1981)], the water-miscible organic solvent addition method in which the solubility of a raw material is increased by the addition of a water-miscible organic solvent [A. Freeman and M. D. Lilly, Appl. Microbiol. Biotechnol., 25, 495 (1987)], and the water-immiscible organic solvent addition or aqueous-organic two-phase system reaction method [M. D. Hocknull and M. D. Lilly, Appl. Microbiol. Biotechnol., 33, 148 (1990)]. In these methods, however it is impossible to avoid the toxicity of raw materials and additives and this makes it difficult to produce the desired substance at high concentrations.

On the other hand, interface bioreactors in which a microorganism grown at the interface between a hydrophilic carrier and a hydrophobic organic solvent is used as a biocatayst are also known. Such interface bioreactors have excellent merits such as an improvement in the soubility of the raw material(s) and product(s), avoidance of the toxicity thereof, ease of product recovery, and abundant oxygen supply from the organic solvent. Moreover, they have the additional advantage of being applicable to essentially all microorganisms and of allowing various reactions such as microbial oxidation, reduction, hydrolysis and esterification to be carried out with good results [S. Oda et al., Biosci. Biotech. Biochem., 56, 2041 (1992); Japanese Patent Laid-Open No. 91878/'93; Japanese Patent Laid-Open No. 344896/'93; Japanese Patent Laid-Open No. 88/'94; Japanese Patent Laid-Open No. 90/'94; Japanese Patent Laid Open No. 95/'94; Japanese Patent Laid-Open No. 197773/'94; Japanese Patent Laid-Open No. 197777/'94].

The above-described interface bioreactors often use agar plates as hydrophilic carriers. Although the construction of a large-scale system is intended in some reports [S. Oda et al., J. Ferment. Bioeng., 78, 149 (1994)], they are still unsatisfactory from a practical point of view. Moreover, they involve the following problem. In the interface bioreactors, owing to the high oxygen-dissolving power of a hydrophobic organic solvent used as the reaction solvent, the microbial reaction proceeds satisfactorily at a significantly lower aeration rate as compared with reactions in an aqueous system. However, they require the use of a large-sized reactor. Especially when its height is increased, it is necessary to equip the reactor with an aeration line. In this case, if air is supplied directly to a reactor in which plate-like carriers are arranged in a horizontal position, a problem arises in that air accumulates between the plate-like carriers to form dead spaces.

SUMMARY OF THE INVENTION

The present inventor made intensive investigations with a view to developing an interface bioreactor which can overcome the above-described problem and which is highly efficient and can be scaled up easily. As a result, it has now be found that the above object can be accomplished by using a reaction tank in which plate-like hydrophilic immobilizing carriers having a microorganism deposited and immobilized on the surfaces thereof in a growable or viable state are arranged in a vertical position and by equipping the reaction tank with a sparger or agitator at the bottom thereof to supply oxygen to the reaction tank and mix the liquid phase present therein. The present invention has been completed on the basis of this finding.

Thus, according to the present invention, there is provided an interface bioreactor system comprising (a) a reaction tank having (1) a reaction solvent placed therein, (2) a plurality of plate-like hydrophilic immobilizing carriers each having a thickness of 1 to 500 mm and packed therein so as to be arranged in a vertical position at intervals of 3 to 100 mm, the hydrophilic immobilizing carriers having a microorganism deposited and immobilized on the surfaces thereof in a growable or viable state and containing a liquid medium containing nutrients necessary for the growth or survival of the microorganism, and (3) a sparger or agitator disposed at the bottom thereof; and (b) an aeration line connected with the reaction tank for supplying oxygen thereto.

According to the present invention, a reaction tank packed with plate-like hydrophilic immobilizing carriers (which may hereinafter be referred to as "plate-like carriers") having a microorganism deposited and immobilized on the surfaces thereof in a growable or viable state is charged with a reaction solvent containing a reaction substrate which is insoluble or slightly soluble in water, and air is supplied to the bottom of the reaction tank for the purpose of supplying oxygen thereto. The supplied air is dispersed by a sparger or agitator disposed at the bottom of the reaction tank to produce small air bubbles, which flow upward through the narrow spaces between the plate-like carriers. This upward flow of the air bubbles produces a satisfactory mixing effect in the reactor packed with the plate-like carriers, so that the supply of oxygen and the reaction substrate to the microorganism can be achieved efficiently.

Thus, a first feature or advantage of the present invention is that the plate-like carriers are arranged in a vertical position and air supplied to the bottom of the reaction tank through the aeration line is forcedly dispersed by injection through a sparger or the rotation of an agitator. As a result, the resulting small air bubbles easily flow upward through the narrow spaces between the carriers. During this process, the flow of the liquid in the spaces between the carriers and the supply of oxygen to the solvent layer are achieved efficiently, eventually enabling oxygen to be efficiently supplied to the microorganism grown on the surfaces of the carriers.

A second feature or advantage of the present invention is that, when the activity of the microorganism is reduced after completion of the reaction, the plate-like carriers having the less active microorganism attached to the surfaces thereof can be regenerated for repeated uses by sterilizing them with steam, washing their surfaces to remove the microbial film therefrom, and then soaking them in a fresh liquid medium to replace the aqueous phase present therein by the fresh liquid medium. Thus, the cost of immobilizing carriers can be reduced markedly.

A third feature or advantage of the present invention is that the lower or upper ends of the plate-like carriers arranged in a vertical position can be kept in contact with a fresh liquid medium so as to cause the aqueous phase present in the internal spaces of the carriers to be continuously or periodically replaced by the fresh liquid medium. This feature consolidates the above-described second feature and, more importantly, enables continuous operation of the system of the present invention. It is known that, as compared with batch operation, continuous operation enhances the productivity of materials. In the system of the present invention, it is possible to arrange the plate-like carriers in a vertical position and keep their lower or upper ends in contact with a liquid medium. Thus, the supply of nutrients and water to the microorganism and the removal of harmful by-products and waste materials can be made to proceed efficiently. This makes it possible to maintain the activity of the microorganism over a long period of time and hence operate the system continuously.

SPECIFIC DESCRIPTION OF THE INVENTION

The interface bioreactor system of the present invention is more specifically described hereinbelow.

No particular limitation is placed on the material of the plate-like hydrophilic immobilizing carriers used in the present invention, so long as they can contain and retain aqueous liquid media containing nutrients for microorganisms. Specific examples thereof include plate-like structures made of natural polymers such as alginate, carrageenan, starch matrix, agar and cellulosic materials (e.g., filter pads); synthetic polymers such as polyvinyl alcohol, urethane polymers, polyacrylamide and polyacrylic acid; and inorganic porous materials such as foam glass plates. Where it is intended to regenerate and use the carriers repeatedly, it is preferable to use plate-like structures made of a gel-like synthetic polymer or an inorganic porous material, because gel-like natural polymers, except filter pads, have the disadvantage of being reduced in strength. Moreover, in order to impart strength thereto, it is preferable to use a tough porous plate (such as filter pad or foam glass plate) or a plate or bar of stainless steel or the like as a skeleton for the carriers. Furthermore, a gel of a natural or synthetic polymer having low strength may be used as a coating on the surfaces of high-strength plate-like structures such as inorganic porous plates.

The interface bioreactor system of the present invention can be applied to any type of microorganism and can be used to carry out various microbial transformation reactions such as oxidation, reduction, hydrolysis and esterification reactions. The microorganism immobilized on the above-described carriers may be any microorganism selected from bacteria, molds, yeasts and actinomycetes, and may be of the aerobic or anaerobic type. Specific examples thereof include microorganisms belonging to the genera Pseudomonas, Gluconobacter, Acetobacter, Arthrobacter, Corynebacterium, Rhodococcus, Alcaligenes, Candida, Hansenula and Aspergillus.

The deposition and immobilization of such microorganisms on the above-described carriers can be performed according to methods which are well known per se, such as those described in the literature including Japanese Patent Laid-Open No. 91878/'93. Finally, the carriers are used in the form of plates.

Specifically, this can be done by depositing a microorganism on the above-described hydrophilic immobilizing carriers, and bringing the microorganism on the carriers into contact with an organic solvent substantially insoluble or slightly soluble in water, in the presence of an aqueous medium containing nutrients for the microorganism, so as to grow the microorganism at the contact interface between the carriers and the organic solvent and thereby form an immobilized microbial phase on the carriers. The organic solvent used for this immobilization may be the same as that used for the preparation of a reaction solvent as will be described later. More specifically, in order to deposit and immobilize a microorganism on the hydrophilic immobilizing carriers, the microorganism is first deposited on the carriers, for example, by applying a suspension of microbial cells to, or spraying it on, the carriers which have previously been impregnated with an aqueous medium containing nutrients, by soaking the a culture of microbial cells, or by causing microbial cells to adhere to the carriers by a suitable means and then supplying the carriers with an aqueous medium containing nutrients. Although the resulting carriers may previously be cultivated in an aqueous medium containing nutrients, they are usually cultivated in contact with an organic solvent containing or not containing an organic compound used as a substrate, so as to grow the deposited microbial cells at the interface between the carriers and the organic solvent and thereby form an immobilized microbial phase on the carriers. This cultivation causes the microorganism to adhere strongly to the surfaces of the carriers, so that the immobilized microbial phase scarcely separates from the surfaces of the carriers.

It is necessary that the internal spaces of the plate-like carriers be filled with an ordinary liquid medium for the cultivation of microorganisms. However, the composition of the liquid medium used receives no particular limitation, but may vary widely according to the type of the microorganism used, and the like. Generally, there may be used liquid media containing carbon sources such as glucose and sucrose; nitrogen sources such as ammonium salts; inorganic salts such as magnesium salts; and minor nutrients such as yeast extract. When a paraffinic hydrocarbon is used as the reaction solvent and also as the substrate for growth, no carbon source need be present in the internal spaces of the carriers.

No particular limitation is placed on the size of the plate-like carriers used in the present invention, so long as they cause no obstruction when packed in the reaction tank. The thickness of the plate-like carriers should be such that they can retain a sufficient amount of liquid medium in the internal spaces thereof and they will not undergo such deformation as to interfere with operation. Specifically, the thickness thereof should be in the range of 1 to 500 mm, preferably 2 to 100 mm, and more preferably 3 to 50 mm.

The interval between adjacent ones of the plate-like carriers arranged in a vertical position within the reaction tank is not critical, so long as the flow of the liquid is not hindered and a solid-liquid interface can be formed between the plate-like carriers and the reaction solvent. Specifically, the interval should be in the range of 3 to 100 mm. Moreover, if consideration is given to productivity and to the stability and uniformity of the flow of the liquid, the interval is preferably in the range of about 4 to 70 mm and more preferably about 5 to 50 mm. The plate-like carriers are preferably mounted on or fixed to a frame of a structure which does not interfere with the flow of the liquid.

The reaction solvent fed to the reaction tank according to the present invention may comprise an organic solvent solution containing a substrate which is insoluble or slightly soluble in water. The organic solvent used for the preparation of the reaction solvent should preferably be one having no toxicity to the immobilized microbial cells. Specific examples thereof include normal paraffins or liquid paraffins typified by hydrocarbons of the methane series having 6 to 20 carbon atoms such as hexane, heptane, octane, nonane and decane; isoparaffins such as isooctane; n-alkylbenzenes having an aliphatic chain of 5 to 15 carbon atoms, such as pentylbenzene, hexylbenzene, heptylbenzene and octylbenzene; isoalkylbenzenes such as cumene; alicyclic hydrocarbons such as cyclohexane; ethers such as hexyl ether; aromatic esters such as dibutyl phthalate; aliphatic esters such as ethyl decanoate; and silicone oils such as polydimethylsiloxane.

Among the foregoing organic solvents, it is preferable to select and use a hydrophobic organic solvent which is substantially harmless to the immobilized particular microorganism.

On the other hand, as the organic compound which is substantially insoluble or slightly soluble in water and serves as a substrate for the microbial transformation (i.e., the reaction substrate), any of various organic compounds may be used without any particular limitation, depending on the transformation capacity of the immobilized microorganism, and the like. Usable organic compounds include, for example, aromatic hydrocarbons such as benzene, toluene, xylene, ethylbenzene, styrene, naphthalene and phenanthrene; aliphatic hydrocarbons such as tridecane and tetradecane; alicyclic compounds such as cyclohexanol and cyclohexanone; heterocyclic compounds such as methylimidazole, collidine and picoline; higher fatty acids such as lauric acid, palmitic acid, stearic acid, oleic acid and linolic acid; higher alcohols such as octyl alcohol, decyl alcohol, lauryl alcohol, cetyl alcohol and stearyl alcohol; and fatty acid esters such as ethyl caprylate and ethyl caproate.

The concentration of the reaction substrate in the above-described organic solvent receives no particular limitation, but may be determined according to the its toxicity to the immobilized microorganism. For example, when the substrate comprises a highly toxic aromatic hydrocarbon as described above, it may be added to normal paraffin composed of hydrocarbons of the methane series having 10 to 15 carbon atoms in an amount of about 5 to 30%. When the substrate comprises a fatty acid ester having relatively low toxicity, it may be added to normal paraffin in an amount of 50% or greater.

Among the foregoing organic compounds, higher fatty acid esters have especially low toxicity and can be used at a concentration of 100% without being mixed with any organic solvent. That is, a higher fatty acid ester itself can be used as an organic solvent coming into contact with the microbial film on the immobilizing carriers and also as a substrate to be converted.

When used as substrates, aliphatic hydrocarbons also have especially low toxicity similarly to higher fatty acid esters. Accordingly, an aliphatic hydrocarbon itself can be used as an organic solvent coming into contact with the microbial phase on the immobilizing carriers and also as a substrate to be converted.

The plate-like carrier-packed interface bioreactor system of the present invention and its operating method are more specifically explained with reference to FIG. 1.

Figure 1:
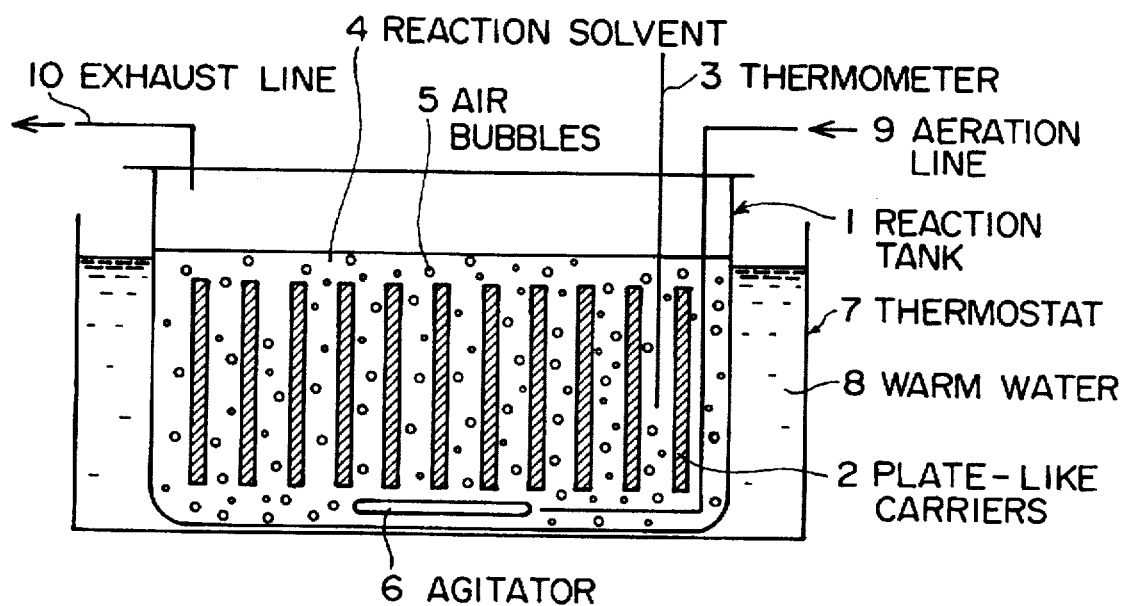
FIG. 1 is a schematic view of an exemplary interface bioreactor system in accordance with the present invention.

This interface bioreactor system basically comprises a reaction tank 1 holding a reaction solvent 4 containing a reaction substrate, having plate-like carriers 2 packed therein, and having an agitator 6 disposed at the bottom thereof; and an aeration line 9 for aerating the reaction solvent 4 within the reaction tank 1. In the reaction tank 1, a plurality of plate-like carriers 2 are arranged in a vertical position by fixing them to a frame (not shown).

Owing to the rotation of the agitator 6 disposed at the bottom of the reaction tank 1, an oxygen-containing gas (e.g., air) supplied through the aeration line 9 is dispersed to produce small air bubbles 5. The extent to which these air bubbles 5 are distributed is determined by the aeration rate, the rotational speed and blade size of the agitator 6. At high rotational speeds of not less than 300 rpm, the air bubbles are widely distributed at the bottom of the reaction tank, so that they spread over a wide range and flow upward through the spaces between the carriers. This wide distribution and upward flow of the air bubbles 5 can improve the efficiency of agitation and mixing of the liquid phase contained in the reaction tank and the efficiency of oxygen supply thereto. In order to further improve the efficiency of agitation and mixing of the liquid contained in the reaction tank, a circulation line (not shown) for circulating the liquid to the outside of the reaction tank may be installed as required. Moreover, an aeration/agitation tower (not shown) may also be installed in order to further improve the efficiency of aeration.

As a result of the aeration, an organic aerosol produced from the reaction solvent 4 may be discharged out of the reaction tank. In order to avoid this, it is preferable to install an oil mist trap in an exhaust line 10.

The collected reaction solvent 4 may be recycled to the reaction tank 1. This can eliminate danger in terms of labor hygiene and safety and, moreover, can prevent losses of the solvent.

In order that the temperature of the reaction solvent within the reaction tank 1 may be kept constant, it is preferable to control the temperature of the reaction tank 1, for example, by fitting the reaction tank 1 with a thermometer 3 and placing it in a thermostat 7 containing warm water 8.

The reaction tank 1 may be equipped with a distilling concentration tower, extraction tank, precipitation tank and/or crystallizer (not shown) required for after-treatment of the desired product recovered from the reaction tank 1. These apparatus can be of any conventional design and may be suitably chosen and used according to the types of the desired product, reaction substrate, reaction solvent and the like.

In the interface bioreactor system of the present invention in which the liquid contained therein (i.e., the reaction solvent) comprises an organic solvent, it is not necessarily required to use stainless steel in the parts which come into contact with the liquid. However, where the inoculation and cultivation of a microorganism on the plate-like carriers are carried out in the interface bioreactor system, the parts of the reaction tank and aeration line which come into contact with the liquid are exposed to water. Consequently, it is preferable to use stainless steel as the material thereof.

The plate-like carriers can be regenerated for repeated uses by washing them after each use and replacing the aqueous phase present in the internal spaces thereof by a fresh liquid medium.

The present invention is further illustrated by the following examples in which the interface bioreactor system of the present invention is used for purposes of microbial transformation.

EXAMPLE 1

A box type reaction tank having an internal capacity of 3 liters was charged with decane as an organic solvent. This reaction tank was packed with 12 plate-like carriers (measuring 13 cm×6 cm and having a thickness of 4 mm) by fixing them to a stainless steel frame (with an interval of 5 mm between adjacent carriers). These carriers had been prepared by growing *Issatchenkia scutulata* var. scutulata IFO 10070 on filter pads (NA-10; manufactured by Advantec-Toyo Co., Ltd., Tokyo) coated with polyvinyl alcohol (PVA-500; manufactured by Kansai Paint Co., Ltd.) for a day. The immobilization of the aforesaid microorganism on the carriers was performed by growing the microorganism in a shake culture for a day by using a liquid medium (pH 6.0) composed of 5 g of peptone, 3 g of malt extract, 3 g of yeast extract, 10 g of glucose, 1 g of magnesium sulfate and 1 liter of water, soaking filter pads in the resulting culture for 10 minutes to inoculate the microorganism thereon, and then removing the filter pads from the broth and subjecting them to a stationary culture on a net for a day.

Thereafter, 50 g of 1-decanol as a raw material for conversion reaction was added to the reaction tank, and the conversion reaction was started at an aeration rate of 300 ml/min and an agitator speed of 500 rpm. For five days after the start of the reaction, samples were taken every day and analyzed for the concentration of the product (i.e., decanoic acid) by gas chromatography. As a result, an accumulation of decanoic acid was observed one day after the start of the reaction, and the five days' reaction yielded 41 g/l of decanoic acid. After completion of the reaction, the reaction solvent was recovered from the reaction tank and about 90% of the organic solvent (i.e., decane) was removed therefrom by vacuum distillation. After the addition of 200 ml of water, the resulting mixture was made alkaline with a 10% aqueous solution of sodium hydroxide so as to recover decanoic acid in the aqueous layer. This aqueous layer was made acidic with 10% hydrochloric acid and then extracted twice with ethyl acetate. The resulting extract was dehydrated with anhydrous magnesium sulfate and freed of ethyl acetate to obtain 37 g of decanoic acid (with a purity of 97% as measured by gas chromatography).

On the other hand, all of the plate-like immobilizing carriers were withdrawn from the reaction tank after completion of the reaction, and sterilized with high-pressure steam in an autoclave. After sterilization, the carriers were washed in vigorously stirred deionized water containing an alkaline detergent to remove the microbial layer from the surfaces thereof, and further washed three times in vigorously stirred deionized water. Thereafter, the carriers were soaked in a fresh liquid medium overnight to replace the water present in the internal spaces thereof by the liquid medium. Using the carriers so prepared, another test for the synthesis of decanoic acid was carried out in the same manner as described above for the first test. As a result, 35 g/l of decanoic acid was obtained.

EXAMPLE 2

A reaction tank similar to that used in Example 1 was charged with 1 liter of dodecane. This reaction tank was packed with 12 plate-like carriers (having a thickness of 4 mm and impregnated with the same liquid medium as used in Example 1) at intervals of 5 mm by means of a stainless steel frame. These carriers had been prepared by growing *Hansenula saturnus* IFO 0809 on filter pads (NA-10; manufactured by Advantec-Toyo Co., Ltd., Tokyo) coated with a photocurable resin (ENTG-3800; manufactured by Kansai Paint Co., Ltd.) which was a copolymer of polyethylene glycol and polypropylene glycol for a day. Thereafter, 50 g of (RS)-citronellol as a raw material for conversion was added to the reaction tank, and a conversion test was carried out for 10 days under the same conditions as employed in Example 1.

Ten days after the start of the reaction, the concentration of the conversion product in the decane layer was determined by gas chromatography. As a result, it was found that the oxidation product [i.e., (S)-citronellic acid] was present in an amount of 23.5 g/l and the residual alcohol [i.e., (R)-citronellol] in an amount of 22.5 g/l. Then, all of the decane layer was recovered and passed through a 30 cm long column packed with silica gel to separate the product by adsorption. Thereafter, (R)-citronellol was eluted from the column with ethyl acetate saturated with aqueous ammonia, and isolated by concentration, washing with water containing saturated NaCl, extraction and drying. Its purity was measured by gas chromatography and, after the formation of a derivative, its optical purity was measured by liquid chromatography (purity, 96%; optical purity, 71% e.e.). Subsequently, (S)-citronellic acid was eluted from the column with methanol-water (1:1), and isolated by concentration, washing with dilute acid, extraction and drying. Its purity was measured by gas chromatography and, after the formation of a derivative, its optical purity was measured by liquid chromatography (purity, 95%; optical purity, 77% e.e.).

What is claimed is:

1. An interface bioreactor system comprising (a) a reaction tank having (1) a reaction solvent placed therein, (2) a plurality of plate-like hydrophilic immobilizing carriers each-having a thickness of 1 to 500 mm and packed therein so as to be arranged in a vertical position at intervals of 3 to 100 mm, said hydrophilic immobilizing carriers having a microorganism deposited and immobilized on the surfaces thereof in a growable or viable state and containing a liquid medium composed of water and nutrients necessary for the growth or survival of the microorganism, and (3) a sparger or agitator disposed at the bottom thereof; and (b) an aeration line connected with said reaction tank for supplying oxygen thereto.

2. A system as claimed in claim 1 wherein said plate-like hydrophilic immobilizing carriers consist of filter pads, gel-like synthetic polymer or an inorganic porous material.

3. A system as claimed in claim 1 wherein said plate-like hydrophilic immobilizing carriers each have a thickness of 3 to 50 mm.

4. A system as claimed in claim 1 wherein said plate-like hydrophilic immobilizing carriers are arranged at intervals of 5 to 50 mm.

5. A system as claimed in claim 1 wherein the reaction solvent comprises as organic solvent solution containing a reaction substrate which is insoluble or slightly soluble in water.

6. A system as claimed in claim 5 wherein the organic solvent is a hydrophobic organic solvent which is substantially harmless to the microorganism.

7. A process for the microbial transformation of a reaction substrate which comprises charging a reaction solvent containing the reaction substrate into the reaction tank of an interface bioreactor system as claimed in claim 1 and carrying out the reaction while supplying air to the bottom of said reaction tank and dispersing the air with a sparger or agitator.

8. A process as claimed in 7 wherein said plate-like hydrophilic immobilizing carriers are regenerated for repeated uses by washing said plate-like hydrophilic immobilizing carriers after each use and replacing the aqueous phase present therein by a fresh liquid medium.

9. A system as claimed in claim 5 wherein said reaction substrate is at least one selected from the group consisting of aromatic hydrocarbons, aliphatic hydrocarbons, alicyclic compounds, heterocyclic compounds, higher fatty acids, higher alcohols and fatty acids esters.

10. A process as claimed in claim 7 wherein said reaction substrate is at least one selected from the group consisting of aromatic hydrocarbons, aliphatic hydrocarbons, alicyclic compounds, heterocyclic compounds, higher fatty acids, higher alcohols and fatty acids esters.

* * * * *